(12) United States Patent
Frank

(10) Patent No.: US 10,184,897 B2
(45) Date of Patent: *Jan. 22, 2019

(54) SYSTEM AND METHOD FOR DETERMINING AN IMPACT OF MANUFACTURING PROCESSES ON THE CALIPER OF A SHEET MATERIAL

(71) Applicant: PACKAGING CORPORATION OF AMERICA, Lake Forest, IL (US)

(72) Inventor: Benjamin Frank, Buffalo Grove, IL (US)

(73) Assignee: Packaging Corporation of America, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/924,677

(22) Filed: Mar. 19, 2018

(65) Prior Publication Data

US 2018/0209914 A1 Jul. 26, 2018

Related U.S. Application Data

(63) Continuation of application No. 14/677,316, filed on Apr. 2, 2015, now Pat. No. 9,952,160.

(60) Provisional application No. 61/975,390, filed on Apr. 4, 2014.

(51) Int. Cl.
| | |
|---|---|
| *B65H 7/20* | (2006.01) |
| *G06T 7/00* | (2017.01) |
| *G01N 21/88* | (2006.01) |
| *B65H 7/14* | (2006.01) |
| *G01N 21/86* | (2006.01) |

(52) U.S. Cl.
CPC .......... *G01N 21/8803* (2013.01); *B65H 7/14* (2013.01); *B65H 7/20* (2013.01); *G01N 21/86* (2013.01); *G06T 7/001* (2013.01); *G06T 2207/10016* (2013.01); *G06T 2207/30164* (2013.01)

(58) Field of Classification Search
CPC ............................. G01N 21/8803; B65H 7/14
See application file for complete search history.

(56) References Cited

U.S. PATENT DOCUMENTS

| | | |
|---|---|---|
| 252,547 A | 1/1882 | Thompson |
| 746,807 A | 12/1903 | Ferres |
| 2,252,585 A | 8/1941 | Swanson |
| 2,300,982 A | 11/1942 | Slagboom |
| 2,674,809 A | 4/1954 | Meienhofer |
| 2,941,573 A | 6/1960 | Cassady |
| 2,944,345 A | 7/1960 | Faeber |
| 3,004,880 A | 10/1961 | Lord |
| 3,064,869 A | 11/1962 | Cooper |
| 3,217,425 A | 11/1965 | Nikkei |
| 3,226,840 A | 1/1966 | Moser |

(Continued)

*Primary Examiner* — Jayanti K Patel
*Assistant Examiner* — Irfan Habib
(74) *Attorney, Agent, or Firm* — Nixon Peabody LLP

(57) ABSTRACT

A method for processing a plurality of sheet material includes receiving a plurality of sheets of material, transporting, via a transport mechanism, the plurality of sheets, one sheet at a time, past a first image capture device, obtaining, via a first image capture device, a first image of a first set of one or more of the plurality of sheets while being transported past the first image capture device, and determining, via at least one processor, a first caliper measurement of the first set of one or more of the plurality of sheets based on the first image of each of the first set.

12 Claims, 5 Drawing Sheets

(56) References Cited

U.S. PATENT DOCUMENTS

| | | | | |
|---|---|---|---|---|
| 3,296,712 | A | 1/1967 | Sachs | |
| 3,319,353 | A | 5/1967 | Matsunami | |
| 3,346,159 | A | 10/1967 | Winkler | |
| 3,349,222 | A | 10/1967 | Johnston | |
| 3,517,164 | A | 6/1970 | Huggins | |
| 3,629,555 | A | 12/1971 | Herbert | |
| 3,712,843 | A | 1/1973 | Gartaganis | |
| 3,726,023 | A | 4/1973 | Geyken | |
| 3,757,081 | A | 9/1973 | Smith | |
| 3,800,434 | A | 4/1974 | Edgington | |
| 3,811,987 | A | 5/1974 | Wilkinson | |
| 3,826,016 | A | 7/1974 | Anderson | |
| 3,864,709 | A | 2/1975 | Bruns | |
| 3,878,622 | A | 4/1975 | Knechtel | |
| 3,895,218 | A | 7/1975 | Cooke | |
| 3,920,496 | A | 11/1975 | Wilkinson | |
| 3,938,261 | A | 2/1976 | Anderson | |
| 3,957,558 | A | 5/1976 | Lee | |
| 3,981,758 | A | 9/1976 | Thayer | |
| 4,086,116 | A | 4/1978 | Yazaki | |
| 4,126,508 | A | 11/1978 | Hoelzinger | |
| 4,128,677 | A | 12/1978 | Hoelzinger | |
| 4,134,781 | A | 1/1979 | Carstens | |
| 4,142,301 | A | 3/1979 | Goodall | |
| 4,161,269 | A | 7/1979 | Kirkpatrick | |
| 4,169,007 | A | 9/1979 | Pray | |
| 4,268,341 | A | 5/1981 | Huhne | |
| 4,306,932 | A | 12/1981 | Bradatsch | |
| 4,316,755 | A | 2/1982 | Flaum | |
| 4,402,778 | A | 9/1983 | Goldsworthy | |
| 4,467,537 | A | 8/1984 | Trotscher | |
| 4,471,214 | A | 9/1984 | Gossler | |
| 4,486,172 | A | 12/1984 | Dunning | |
| 4,526,634 | A | 7/1985 | Beer | |
| 4,544,597 | A | 10/1985 | Peer | |
| 4,552,781 | A | 11/1985 | Cannady | |
| 4,655,163 | A | 4/1987 | Hokenson | |
| 4,662,554 | A | 5/1987 | Yamazaki | |
| 4,764,236 | A | 8/1988 | Nikkei | |
| 4,806,183 | A | 2/1989 | Williams | |
| 4,806,733 | A | 2/1989 | Stone | |
| 4,871,406 | A | 10/1989 | Griffith | |
| 4,887,362 | A | 12/1989 | Rautakorpi | |
| 4,889,580 | A | 12/1989 | Seki | |
| 5,004,891 | A | 4/1991 | Landis | |
| 5,013,403 | A | 5/1991 | Chase | |
| 5,049,216 | A | 9/1991 | Shead | |
| 5,094,394 | A | 3/1992 | Saukkonen | |
| 5,146,097 | A | 9/1992 | Fujiwara | |
| 5,181,330 | A | 1/1993 | Schoch | |
| 5,244,518 | A | 9/1993 | Krayenhagen | |
| 5,249,373 | A | 10/1993 | Rogne | |
| 5,256,240 | A | 10/1993 | Shortt | |
| 5,292,391 | A | 3/1994 | Wallick | |
| 5,348,610 | A | 9/1994 | McKinlay | |
| 5,437,752 | A | 8/1995 | Lang | |
| 5,456,783 | A | 10/1995 | Sissons | |
| 5,458,051 | A | 10/1995 | Alden | |
| 5,466,329 | A | 11/1995 | Marschke | |
| 5,467,695 | A | 11/1995 | Keller | |
| 5,495,092 | A | 2/1996 | Marschke | |
| 5,498,304 | A | 3/1996 | Shaw | |
| 5,501,762 | A | 3/1996 | Marschke | |
| 5,561,918 | A | 10/1996 | Marschke | |
| 5,578,160 | A | 11/1996 | Krznarich | |
| 5,837,974 | A | 11/1998 | Sissons | |
| 5,853,543 | A | 12/1998 | Hu | |
| 6,006,602 | A | 12/1999 | Preston | |
| 6,064,759 | A * | 5/2000 | Buckley | G01B 11/024 348/125 |
| 6,099,690 | A | 8/2000 | Hu | |
| 6,236,735 | B1 * | 5/2001 | Bjorner | G06K 9/2018 250/559.44 |
| 6,327,333 | B1 * | 12/2001 | Uchida | G01M 17/028 378/58 |
| 6,461,035 | B2 * | 10/2002 | Meinlschmidt | G01N 25/72 356/237.2 |
| 6,517,679 | B1 | 2/2003 | Mustonen | |
| 6,519,534 | B2 | 2/2003 | Chen | |
| 6,712,936 | B2 | 3/2004 | Hamad | |
| 7,090,134 | B2 * | 8/2006 | Ramsager | B07C 3/18 235/454 |
| 7,321,425 | B2 | 1/2008 | Haran | |
| 7,367,592 | B1 * | 5/2008 | Puttkammer | D21F 1/44 162/110 |
| 7,513,964 | B2 * | 4/2009 | Ritter | G01N 25/72 156/64 |
| 7,561,717 | B2 * | 7/2009 | Anderson | G06K 17/0022 235/462.13 |
| 7,688,447 | B2 | 3/2010 | Shakespeare | |
| 7,709,794 | B2 * | 5/2010 | Zhao | G01N 25/72 250/334 |
| 7,769,223 | B2 * | 8/2010 | Shinohara | G01N 21/896 348/125 |
| 7,809,158 | B2 * | 10/2010 | Carpenter | B07C 1/04 209/584 |
| 7,855,348 | B2 * | 12/2010 | Goodwin | G06K 9/2018 209/584 |
| 7,880,156 | B2 | 2/2011 | Shakespeare | |
| 8,017,927 | B2 | 9/2011 | Shakespeare | |
| 8,176,524 | B2 | 5/2012 | Singh | |
| 8,189,686 | B2 | 5/2012 | Boyes | |
| 8,220,796 | B2 * | 7/2012 | Takahata | B65H 29/70 271/188 |
| 8,246,046 | B2 * | 8/2012 | Taniyama | G07D 11/0039 271/258.01 |
| 8,313,605 | B2 | 11/2012 | Yamamoto | |
| 8,463,560 | B2 | 6/2013 | Allan | |
| 8,526,745 | B2 | 9/2013 | Liu | |
| 8,618,929 | B2 | 12/2013 | Ganapathy | |
| 8,665,967 | B2 | 3/2014 | Ngo | |
| 8,750,732 | B2 | 6/2014 | Ishii | |
| 8,774,270 | B2 | 7/2014 | Park | |
| 8,877,010 | B2 | 11/2014 | Saren | |
| 8,994,817 | B2 * | 3/2015 | Heintze | G01N 25/72 152/251 |
| 9,071,849 | B2 | 6/2015 | Yoon | |
| 9,110,035 | B2 * | 8/2015 | Zheng | G01N 21/896 |
| 9,277,057 | B2 | 3/2016 | Rabipour | |
| 9,633,278 | B2 * | 4/2017 | Mase | G06K 9/4671 |
| 9,646,369 | B2 * | 5/2017 | Salzman | G06T 7/0004 |
| 2003/0123659 | A1 | 7/2003 | Forstrom | |
| 2004/0250969 | A1 * | 12/2004 | Luu | B32B 23/10 162/123 |
| 2006/0098190 | A1 * | 5/2006 | Miyake | G01N 21/896 356/239.1 |
| 2007/0202843 | A1 | 8/2007 | Niu | |
| 2008/0002894 | A1 | 1/2008 | Hayon | |
| 2008/0083519 | A1 * | 4/2008 | Kokko | D21F 11/14 162/9 |
| 2008/0210396 | A1 | 9/2008 | Hellstrom | |
| 2008/0300825 | A1 | 12/2008 | Ishibuchi | |
| 2009/0021751 | A1 * | 1/2009 | Jonasson Bjarang | B07C 5/3425 356/601 |
| 2009/0255387 | A1 * | 10/2009 | Pelletier | B26D 5/32 83/13 |
| 2010/0158310 | A1 * | 6/2010 | McQueen | G06K 9/00 382/100 |
| 2010/0284608 | A1 * | 11/2010 | Monti | G06K 9/6211 382/154 |
| 2011/0135573 | A1 * | 6/2011 | Devy | C07K 16/40 424/9.1 |
| 2012/0194668 | A1 * | 8/2012 | Kim | G01N 21/21 348/135 |
| 2012/0222798 | A1 * | 9/2012 | Nakamura | B32B 5/26 156/164 |
| 2013/0223673 | A1 * | 8/2013 | Davis | G06K 9/78 382/100 |
| 2013/0279606 | A1 | 10/2013 | Vanam | |
| 2013/0289918 | A1 | 10/2013 | Haran | |

(56) References Cited

U.S. PATENT DOCUMENTS

2013/0329037 A1* 12/2013 Shakespeare .......... B65H 43/00
                                                    348/88
2014/0092997 A1    4/2014  Zhou
2014/0253912 A1*  9/2014  Honda ................. G01N 21/956
                                                    356/237.5

* cited by examiner

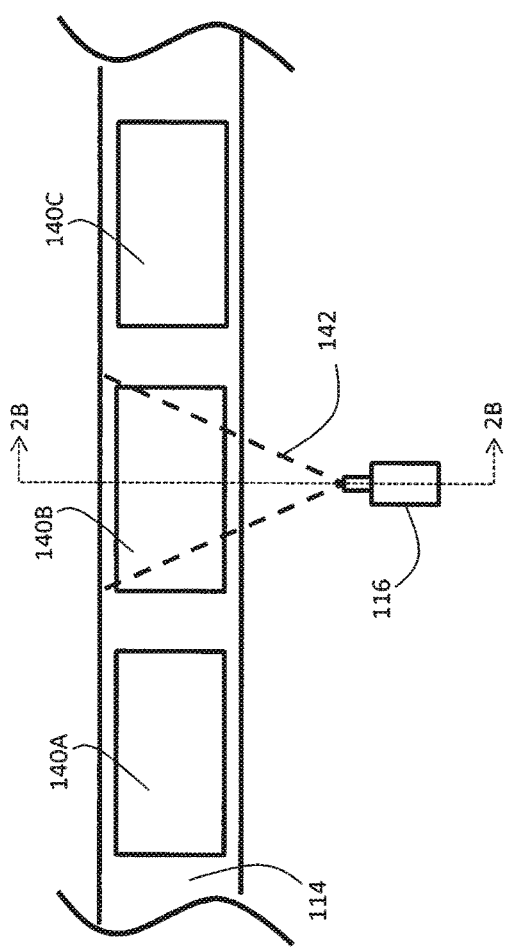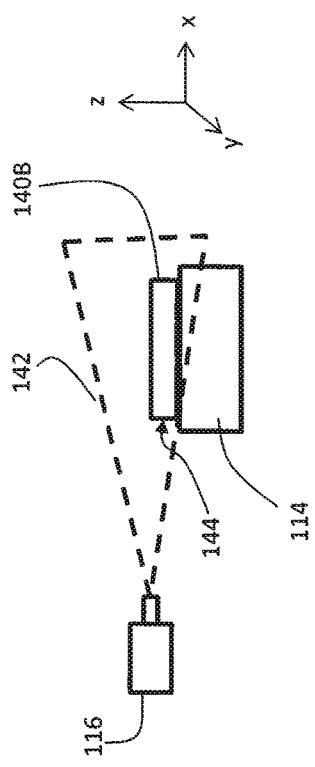

SYSTEM AND METHOD FOR DETERMINING AN IMPACT OF MANUFACTURING PROCESSES ON THE CALIPER OF A SHEET MATERIAL

CLAIM OF PRIORITY AND CROSS-REFERENCE TO RELATED APPLICATIONS

This application is a continuation of U.S. patent application Ser. No. 14/677,316 filed on Apr. 2, 2015, which has been allowed, and claims the benefit of priority to U.S. Provisional Patent Application No. 61/975,390, which was filed on Apr. 4, 2014, and is incorporated herein by reference in their entireties and for all purposes.

TECHNICAL FIELD

The present disclosure relates generally to the manufacture of sheet material products. In particular, aspects of the present disclosure relate to systems, devices and processes for determining an impact of one or more manufacturing processes on a caliper of a sheet material.

BACKGROUND

Caliper (thickness) measurement can be critical for understanding process impacts in the act of creating products made from sheet materials. For example, in the context of a box product made from a corrugated fiberboard sheet material, the caliper of the sheet material correlates with board stiffness and load carrying capacity and, thus, box performance characteristics. For that reason, it is a critical process parameter in the manufacture of such products. Similarly, caliper is an important process parameter that is considered in the manufacture of other products from sheet materials, such as, for example, paper, paperboard, corrugated fiberboard, plastic, corrugated plastic, combinations thereof, and/or the like.

Conventionally, caliper measurement is a manual process. As sheet material is being processed, for example, a small number of sheets are removed and manually measured by a caliper device or, in some instances, by destructive testing. For instance, to manufacture a corrugated box container, manual measurements are typically obtained at a corrugator once combined board is formed, again before that combined board is converted into a box, and finally once the manufacture of the box has been completed. This process is labor intensive and time consuming. As such, only a limited number of products can be inspected. Indeed, it is not uncommon for an entire run of thousands of boxes to be characterized by one or, at most, a handful of caliper measurements to assess the impact of the process on the corrugated board from which the boxes are made.

Past attempts to improve the process of measuring caliper have been largely unsuccessful for a number of reasons. Generally, such attempts required restraint of the sheet material against a fixed and stable portion of an apparatus (e.g., to align the sheet with a measurement device and/or provide a reference point from which to measure). Yet, the process of restraining the sheet materials introduces substantial inefficiencies (i.e., significantly slowed processing speeds) and risks additional damage to the sheet material from the restraining contact. Other attempts to measure caliper of sheets in motion were generally frustrated by the frequent and erratic movement of the sheets along the transport path due to, for example, vibrations, mechanical processing impacts, aerodynamics, etc.

SUMMARY

According to aspects of the present disclosure, systems are presented for processing sheet materials. In an implementation, the system includes an input configured to receive one or more sheets of material, an output, and a transport mechanism configured to transport the one or more sheets, one sheet at a time, from the input along a transport path to the output. The system also includes a manufacturing process device that is disposed along the transport path and is configured to change each of the one or more sheets from a first state to a second state. The system further includes a first image capture device. The image capture device can be located, for example, along the transport path, e.g., proximate the input, the manufacturing process device, the output, or any combination thereof. The first image capture device is configured to obtain one or more first images. Each of the first images is of at least one of the one or more sheets. The system also includes at least one processor that is communicatively coupled to the first image capture device. The at least one processor is configured to determine process-impact information based on one or more first images, including at least a caliper measurement of each of the at least one of the one or more sheets.

According to additional aspects of the present disclosure, systems for processing a plurality of sheets of material are disclosed. In an implementation, the system includes an input area or receptacle that is configured to receive a plurality of sheets of material, and an output area or receptacle that is configured to receive one or more sheets of material. A transport mechanism is configured to transport the sheets, e.g., one sheet at a time, from the input area/receptacle along a transport path to the output area/receptacle. The system also includes one or more manufacturing process devices disposed along the transport path. Each manufacturing process device is configured to apply a manufacturing process to at least one of the sheets. The system further includes a first image capture device located at or between the input area/receptacle and one of the manufacturing process devices. The first image capture device is configured to obtain a first image of a first set of the plurality of sheets. The system further includes a second image capture device located at or between one of the manufacturing process devices and the output area/receptacle. The second image capture device is configured to obtain a second image of a second set of the plurality of sheets. At least one processor is communicatively coupled to the first image capture device and the second image capture device. The at least one processor is configured to determine a first caliper measurement for each of the sheets in the first set of the sheets based on the first images, and determine a second caliper measurement for each of the sheets in the second set of sheets based on the second images.

According to additional aspects of the present disclosure, methods for processing sheet material are disclosed. A method for processing a plurality of sheet material includes, for example, receiving a plurality of sheets of material; transporting, via a transport mechanism, the sheets of material, one sheet at a time, past a first image capture device; obtaining, via a first image capture device, a first image of a first set of one or more of the sheets while being transported past the first image capture device; and, determining, via at least one processor, a first caliper measurement of the first set of one or more sheets based on the first image of each sheet of the first set.

The above summary is not intended to represent every embodiment or every aspect of the present disclosure. Rather, the foregoing summary merely provides an exemplification of some of the novel aspects and features set forth herein. The above features and advantages, and other features and advantages of the present disclosure, which are considered to be inventive singly or in any of various combinations, will be readily apparent from the following detailed description of representative embodiments and modes for carrying out the present invention when taken in connection with the accompanying drawings and the appended claims.

BRIEF DESCRIPTION OF THE DRAWINGS

FIGS. 2A and 2B are plan-view and side-view illustrations, respectively, of an exemplary section of the sheet processing system illustrated in FIG. 1.

Figure 1:
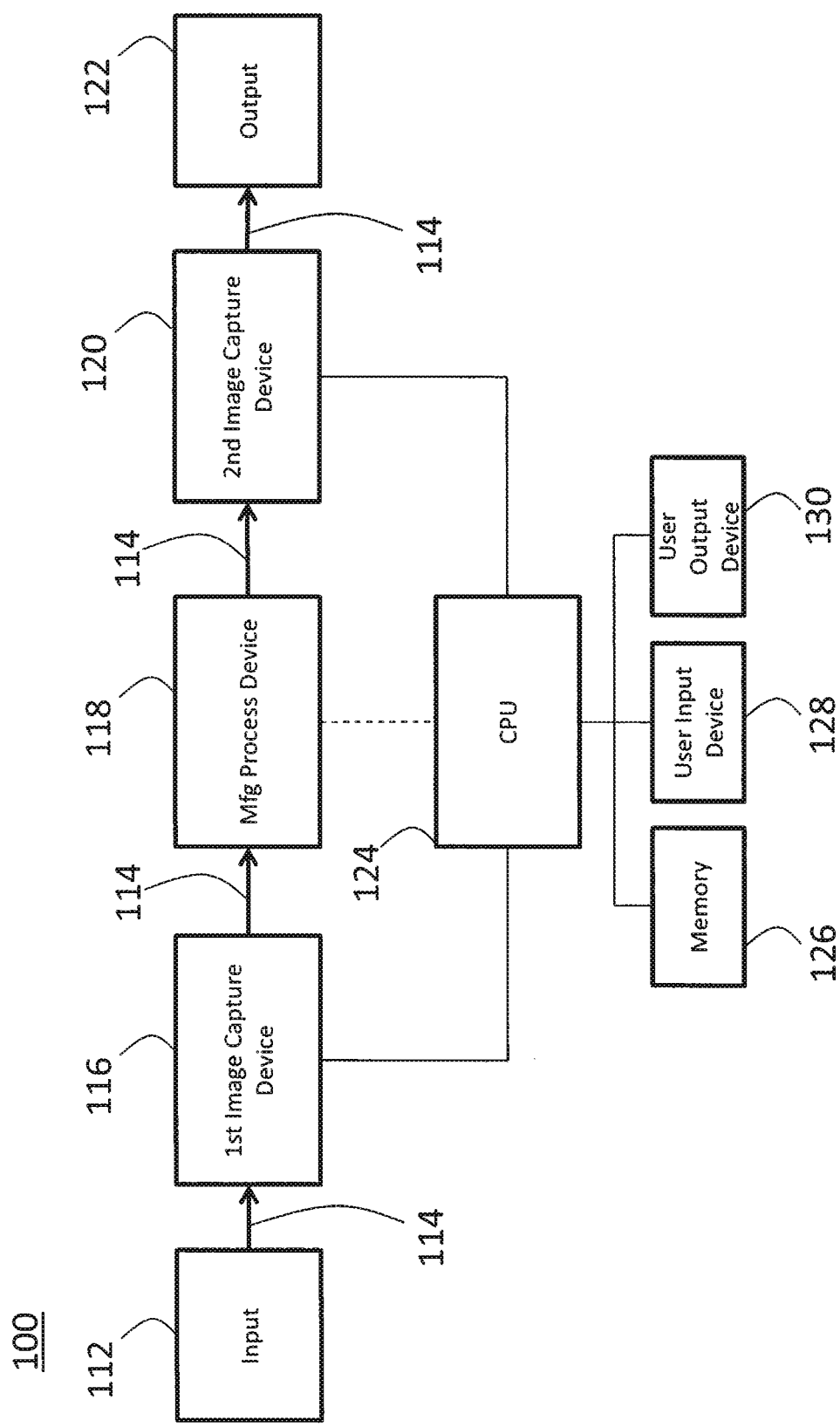
FIG. 1 is a diagrammatic illustration of an example of a sheet processing system according to aspects of the present disclosure.

While the present disclosure is susceptible to various modifications and alternative forms, some representative embodiments thereof have been shown by way of example in the drawings and will herein be described in detail. It should be understood, however, that the inventive aspects are not limited to the particular forms illustrated in the drawings. Rather, the disclosure is to cover all modifications, equivalents, combinations, and alternatives falling within the spirit and scope of the invention as defined by the appended claims.

DETAILED DESCRIPTION OF THE ILLUSTRATED EMBODIMENTS

This disclosure is susceptible of embodiment in many different forms. There are shown in the drawings, and will herein be described in detail, representative embodiments with the understanding that the present disclosure is to be considered as an exemplification of the principles of the present disclosure and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference or otherwise. For purposes of the present detailed description, unless specifically disclaimed or logically prohibited: the singular includes the plural and vice versa; and the words "including" or "comprising" or "having" means "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

In the following description of the exemplary systems and methods, the sheet material is described as corrugated fiberboard; however, it should be understood that the sheet material can alternatively be other materials such as, for example, paper, paperboard, plastic, corrugated plastic, combinations thereof, and/or the like. The systems and methods of the present disclosure address problems that have long been without a viable solution. Namely, the systems and methods of the present disclosure achieve measurement of the caliper of sheet materials while being transported at high rates of speed through manufacturing process systems. The sheet materials do not need to be removed, damaged, restrained, or contacted in any way to achieve such caliper measurements. Advantageously, the systems and methods of the present disclosure allow for the collection and analysis of large sample sizes, providing a more robust and comprehensive understanding of the sheet materials being processed and/or the impact of various manufacturing processes on the sheet materials. Indeed, in some instances, the systems and methods of the present disclosure can provide real-time or near real-time monitoring of the caliper of portions or all of the sheet materials being processed.

FIG. 1 illustrates an exemplary schematic diagram of a system 100 for processing sheet materials according to aspects of the present disclosure. As shown in FIG. 1, the system 100 includes an input receptacle 112, a transport mechanism 114, a first image capture device 116, a manufacturing process device 118, a second image capture device 120, and an output receptacle 122. The system 100 can further include a controller 124, a memory 126, a user input device 128, and a user output device 130.

The input receptacle 112 is configured to receive a plurality of sheets of corrugated board (i.e., corrugated fiberboard). As one non-limiting example, the plurality of sheets of corrugated board can be received in the input receptacle 112 as a stack. The transport mechanism 114 is configured to transport the sheets of corrugated board, one sheet at a time, from the input receptacle 112 to the output receptacle 122 via the first image capture device 116, the manufacturing process device 118, and the second image capture device 120. That is, the first image capture device 116, the manufacturing process device 118, and the second image capture device 120 are disposed along a transport path between the input receptacle 112 and the output receptacle 122. As one non-limiting example, the transport mechanism 114 can include one or more conveyor belts, rollers, etc. The output receptacle 122 is configured to receive the plurality of sheets of corrugated board once processed (e.g., as a stack of sheets).

The manufacturing process device 118 includes one or more devices that are configured to manufacture aspects of a corrugated board product (e.g., a box blank or a fully-assembled box) from the corrugated board sheets. For example, the manufacturing process device 118 can be configured to cut, score, crush, print, glue, staple, tape, and/or wire stitch one or more portions of each sheet of corrugated board. In one non-limiting implementation, the manufacturing process device 118 can be flexo folder gluer. In another non-limiting implementation, the manufacturing process device 118 can include one or more sections of a flexo folder gluer (e.g., a feed section, a printing section, a creaser-slotter section, an in-line die cutter, a glue lap unit, a folding section, etc.). Stated more generally, the manufacturing process device 118 can include one or more devices configured to change each sheet from a first state to a second state.

The first image capture device 116 and the second image capture device 120 are configured to obtain a first image and a second image, respectively, of one or more of the sheets of corrugated board as the sheets are transported past the first image capture device 116 and the second image capture device 120. More particularly, the first image capture device 116 and the second image capture device 120 are configured to obtain the first image and the second image, respectively, of a thickness of the sheet(s) (i.e., in a dimension defined by the walls and flute(s) of the corrugated board, as should be understood by a skilled artisan). For example, the first image capture device 116 and the second image capture device 120 can be located with respect to the transport mechanism 114 such that a lateral side of each sheet passes through a field of view of the first image capture device 116 and a field of view of the second image capture device 120 as it is being transported along the transport path.

According to some aspects, the first image capture device 116 can be located on either side of the transport path such that, for example, the sheets are generally coplanar with the field of view of the first image capture device 116 and the field of view of the second image capture device 120. According to some aspects, the first image capture device 116 and the second image capture device 120 can be respectively oriented such that the field of views of the first image capture device 116 and the second image capture device 120 are generally orthogonal to the transport path at the respective locations of the first image capture device 116 and the second image capture device 120. According to other aspects, the first image capture device 116 and the second image capture device 120 can be oriented at non-orthogonal angles (e.g., oblique angles) relative to the transport path.

As one non-limiting example, FIGS. 2A and 2B illustrate an exemplary configuration of the first image capture device 116 relative to the transport mechanism 114. FIG. 2A shows a plurality of sheets 140A-140C located on a portion of the transport mechanism 114 near the first image capture device 116. As shown in FIG. 2A, the sheet 140B is passing through a field of view 142 of the first image capture device 116. FIG. 2B is a sectional view taken through the line 2B-2B shown in FIG. 2A. As shown in FIG. 2B, the first image capture device 116 is located on a side of and generally coplanar to the transport mechanism 114 and oriented generally orthogonal to the transport mechanism 114 such that a lateral side 144 of the sheet 140B is located within the field of view 142 of the first image capture device 116. As described above, it is contemplated that other locations and orientations can be employed (e.g., such that a leading lateral side of the sheet 140B can be positioned within the field of view 142).

Additionally, as shown in FIG. 2B, the first image capture device 116 is configured such that the sheets 140A-140C can pass through the field of view 142 despite any potential movement in the z-direction due to, for example, vibrations, mechanical processing impacts, aerodynamics, etc. For example, the first image capture device 116 can be located at a distance from the transport mechanism 114 based on the optical characteristics of the first image capture device 116 (e.g., lens size, focal length, aperture size, etc.) to allow for movement of the sheets in the z-direction during transport past the first image capture device 116.

According to some aspects of the present disclosure, the first images and the second images can include an image of only a single sheet (or a portion thereof) at a time. According to alternative aspects of the present disclosure, the first images and the second images can include an image of one or a plurality of sheets (or portions thereof) at a time.

The first image capture device 116 and the second image capture device 120 are communicatively coupled to the controller 124. In particular, the first image capture device 116 and the second image capture device 120 are configured to transmit image information (e.g., via wired or wireless communication signals) indicative of the first and second images obtained by the first image capture device 116 and the second image capture device 120. The controller 124 is configured to process the image information received from the first image capture device 116 and the second image capture device 120.

According to aspects of the present disclosure, the controller 124 is programmed to determine a caliper measurement for each sheet shown in the first images and second images. In this way, the controller 124 can continuously or repeatedly monitor the caliper of the sheets of corrugated board as the sheets are transported through the system 100. As one non-limiting example, the controller 124 can run an image analysis program on the first images and second images, utilizing edge detection algorithms, to determine a caliper measurement for each sheet shown in the first images and the second images. That is, the controller 124 can be programed to detect changes in image brightness to determine the lower edge and the upper edge of a sheet. The caliper measurement can thus be determined from the distance between the detected upper edge and the detected lower edge of the imaged sheet. In implementations in which a first image and/or a second image may include a plurality of sheets (or portions thereof), the controller 124 can be configured to employ additional image processing algorithms to further distinguish one sheet from another when multiple sheets are captured within a first image or a second image.

It is contemplated that, according to some aspects, the controller 124 can be configured to run a calibration program to facilitate translation of the distance between the lower edge and the upper edge of each image to a caliper measurement (e.g., the calibration determines a scaling factor for converting a image distance or number of pixels between to the caliper measurement of the sheet). According to additional and/or alternative aspects, the first image capture device 116 and the second image capture device 120 can be configured according to predetermined conditions (i.e., location, orientation, distance from the sheets on the transport mechanism 114, etc.) to facilitate translation of the determined image distance to the caliper measurement.

According to aspects of the present disclosure, the controller 124 can be configured to compare the determined caliper measurements to a predetermined tolerance range (and/or a predetermined threshold value). The controller 124 can be further configured to generate an error signal based on the comparison. For example, the controller 124 can be configured to generate an error signal if any caliper measurement is outside of the tolerance range. As another example, the controller 124 can be configured to generate an error signal if more than a threshold number of caliper measurements are outside of the tolerance range. As yet another example, the controller 124 can be configured to generate an error signal if more than a threshold percentage of the caliper measurements are outside of the tolerance range. The controller 124 can thus be configured to determine whether an error condition exists based on the comparison of the determined caliper measurement(s) to error checking criteria. According to aspects of the present disclosure, process-impact is determined by the controller 124 by comparing the determined caliper measurements, e.g., determined from the images taken by the first image capture device, to a previously measured set of satisfactory caliper measurements.

According to some aspects, the error signal can include an indication as to whether the error condition is associated with a first image or a second image. As such, the error signal can provide information as to the nature of a problem with the system 100. For example, a caliper measurement determined from a first image to be outside of the tolerance range may indicate a problem with the sheets being fed into the system 100 while a caliper measurement determined from a second image to be outside of the tolerance range may indicate that the manufacturing process device 118 detrimentally impacted the sheets during processing. It is contemplated that, according to some aspects, the controller 124 can be configured to compare caliper measurements from the first images to a first tolerance range and caliper measures from the second images to a second tolerance range. This may be useful for implementations in which it is expected and/or intended that the manufacturing process device 118 will impact the caliper of the sheets to a certain extent.

As the first image capture device 116 is located before the manufacturing process device 118 and the second image capture device 120 is located after the manufacturing process device 118 along the transport path, the controller 124 can be additionally and/or alternatively configured to quantify and evaluate the impact of the manufacturing process device 118 on the sheets by determining a change in the caliper measurements based on one or more of the first images and the second images.

According to some aspects of the present disclosure, the controller 124 can be configured to determine a change in caliper measurement based on a first image and a second image of the same sheet. For example, a first caliper measurement of a sheet can be determined from a first image, a second caliper measurement of the same sheet can be determined from a second image, and the change in caliper measurement can thus be determined by the difference between the first caliper measurement and the second caliper measurement. In some implementations, the controller 124 can be configured to control the first image capture device 116 and the second image capture device 120 such that the first image and the second image are obtained at times at which it is known that the target sheet is located within the respective fields of view of the first image capture device 116 and the second image capture device 120. In one example, the controller 124 can be configured to control image capture timing based on known transport speeds of the transport mechanism 114 and the distance between the first image capture device 116 and the second image capture device 120. In another example, sensors (not shown) may be employed to detect the presence and/or number of sheets passing through the field of views of the first image capture device 116 and the second image capture device 120.

According to additional and/or alternative aspects of the present disclosure, the controller 124 can be configured to determine the change in caliper measurement based on any first image and any second image regardless of whether the first image and the second image are of the same sheet. For example, a first caliper measurement of a first sheet can be determined from a first image, a second caliper measurement of a second sheet (which may be the same or different from the first sheet) can be determined from a second image, and the change in caliper measurement can thus be determined by the difference between the first caliper measurement and the second caliper measurement. While determining a change in caliper measurement based on measurements for the same sheet provides a more direct indication of the effect of a manufacturing process device 118 on the caliper of the sheet, determining a change in caliper measurement based on measurements from any sheet (i.e., same or different sheet) can still provide an informative and useful indication of the effect of the manufacturing process device 118 while minimizing system resource requirements needed to control the timing of the image capture devices 116, 120 and/or track the identity of the sheets transported through the system 100.

According to still additional and/or alternative aspects of the present disclosure, the controller 124 can be configured to determine an average change in caliper measurement based on caliper measurements derived from a plurality of first images and a plurality of second images. For example, the controller 124 can be configured to determine the change in caliper as the difference between an average caliper measurement for sheets shown in a plurality of first images and an average caliper measurement for sheets shown in a plurality of second images. In some instances, the plurality of first images and the plurality of second images can include images of the same plurality of sheets and, in other instances, the plurality of first image and the plurality of second images may not be images of the same sheets (i.e., at least one sheet is different between the first images and the second images). The average change in caliper measurement can thus provide additional and/or alternative data for determining the impact of the manufacturing process device 118 on the caliper of the sheets transported through the system 100.

The controller 124 can be configured to evaluate the determined change in caliper measurement(s) (or average thereof) to determine if an error condition exists. For example, the determined change in caliper measurement(s) can be compared to a predetermined tolerance range or predetermined threshold value(s) in a manner similar to that described above for evaluation of a caliper measurement with respect to a tolerance range. Additionally, as described above, the controller 124 can be further configured to generate an error signal based on such comparisons to the tolerance range(s) and/or threshold value(s).

According to some aspects of the present disclosure, a first image and a second image can be obtained for each sheet transported through the system 100. This approach may allow for a comprehensive analysis of the effects of the manufacturing process on all sheets transported through the system. Notably, such functionality has not previously been achieved as prior systems and methods for the manufacture of sheet materials can only measure limited sample sizes due to the labor intensive process of manual measurement or the need to restrain the sheet material from movement during measurement. According to alternative aspects of the present disclosure, a first image and a second image can be obtained for some but not all of the sheets transported through the system. While small sample sizes may be utilized for analysis by the controller 124, the system 100 can be advantageously configured to process larger amounts of data than could previously be processed via prior systems and methods for the manufacture of sheet material products.

According to some aspects of the present disclosure, the caliper measurement(s) and/or the determined change in caliper measurement(s) (or averages thereof) can be stored as process-impact information in the memory 126. The process-impact information may be viewed by a user via the user output device 130. In some non-limiting implementations, the process-impact information can be stored in the memory 126 with identification information associated with the sheet(s) from which the process-information is derived. For example, the controller 124 can be configured to assign a unique identifier to each sheet imaged in the first images and the second images, which may be stored with the process-impact information in the memory 126.

Optionally, the controller 124 can be further configured to control the operation of the manufacturing process device 118. For example, the controller 124 can be configured to transmit a control signal, which when received, causes the manufacturing process device 118 to stop, start, and/or adjust a manufacturing process applied to the sheets transported through the system 100. In some non-limiting implementations, the control signals can be generated in response to inputs received from a user via the user input device 128. In additional and/or alternative implementations, the control signals can be automatically generated based on the controller 124 processing the process-impact information (e.g., based on comparisons to one or more predetermined threshold values and/or tolerance ranges). In instances in which the controller 124 can adjust the manufacturing process applied by the manufacturing process device 118, a feedback system can be formed whereby the controller 124 can continuously or repeatedly monitor the process-impact information to make further adjustments until the process-impact information conforms to the desired manufacturing tolerance requirements or criteria.

It should be understood that the system 100 illustrated and described for FIG. 1 is intended to be exemplary and that the system 100 can be modified to include additional components, fewer components, and/or modified components. For example, while the exemplary system 100 illustrated in FIG. 1 includes an input receptacle 112 and an output receptacle 122 that are configured to receive a plurality of sheets, the input receptacle 112 and/or the output receptacle 122 can be configured to receive only one sheet at a time for facilitating ingress and egress of the sheets for the system 100. Additionally, for example, while the exemplary system 100 includes two image capture devices 116, 120, it is contemplated that the system 100 can include any number (i.e., one or more) image capture devices 116, 120 according to alternative aspects of the present disclosure.

Caliper measurements taken by the image capture devices 116, 120 and CPU 124 may be subject to a minimum resolution requirement. For at least some implementations, a particular point of interest is changes in caliper through a process, which can require determining a difference measurement between an initial caliper and a final caliper. Because differences as small as one one-thousandth of an inch can indicate meaningful process impact to the material, it is desirable, for example, that the minimum resolution requirement be at least approximately one one-thousandth of an inch. Optionally, the minimum resolution requirement is an order of magnitude better than the significance level for the measurement itself, indicating an optimal resolution of one tenth of one-thousandth of an inch. This can help to clearly distinguish process changes as a corrugated sheet traverses, for example, a flexo. While resolution between these levels can still be contributory, once resolution becomes less precise than the higher value (0.001"), the ability to identify meaningful impacts is severely constrained.

Figure 3:
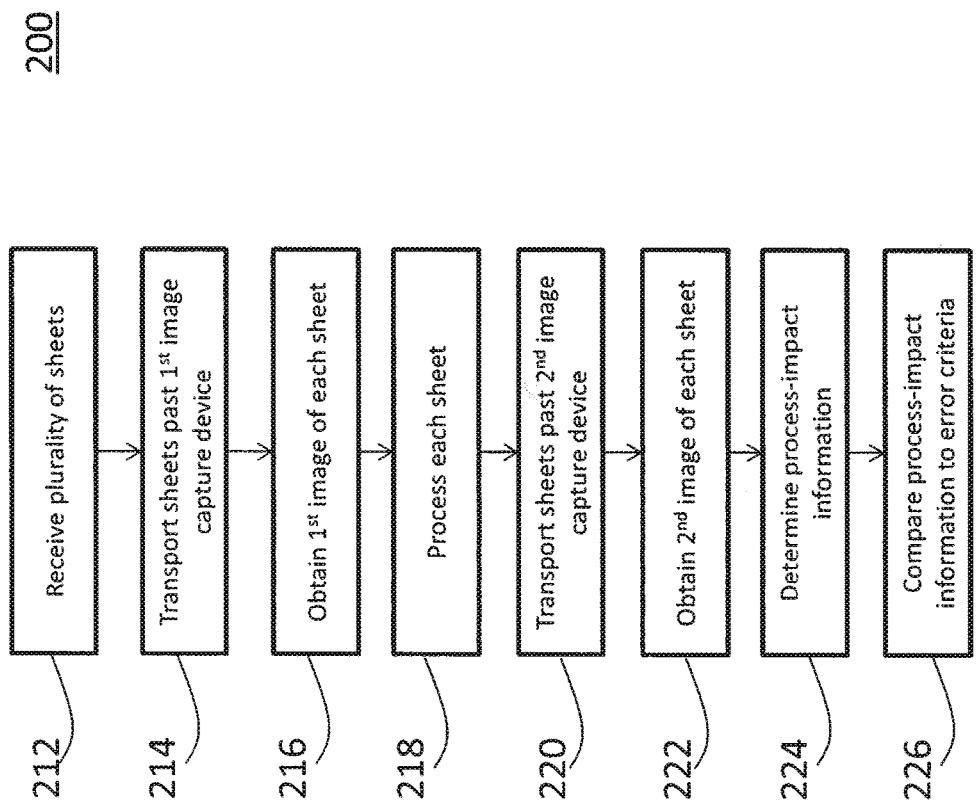
FIG. 3 is a flowchart of a representative workflow process for determining an impact of a manufacturing process according to aspects of the present disclosure.

Referring now to FIG. 3, an exemplary flowchart for a method 200 of processing a plurality of sheets (e.g., sheets of corrugated fiberboard, paper, paperboard, plastic, corrugated plastic, combinations thereof, and/or the like) is illustrated. At step 212, a plurality of sheets are received (e.g., in the input receptacle 112). At step 214, the sheets are transported (e.g., via the transport mechanism 114), one at a time, past the first image capture device 116. At step 216, a first image of one or more sheets is obtained by the first image capture device 116. After the first image is obtained at step 216, the sheets are processed, for example, by a manufacturing process device 118 at step 218. As described above, the manufacturing process device 118 can cause the sheets to change from a first state (e.g., unprinted, uncut, unscored, etc.) to a second state (e.g., printed, cut, scored, etc.). At step 220, after the sheets have been processed, the sheets are transported past the second image capture device 120. At step 220, a second image of one or more sheets is obtained by the second image capture device 120. At step 224, the process-impact information is determined based on the first image(s) and/or the second image(s) obtained at steps 216 and 222. Optionally, at step 226, the process-impact information is compared to error checking criteria (e.g., a predetermined threshold and/or tolerance range).

FIG. 3, described by way of example above, represents one algorithm that corresponds to at least some instructions executed by the controller 124 in FIG. 1 to perform the above described functions associated with the described concepts. It is also within the scope and spirit of the present concepts to omit steps, include additional steps, and/or modify the order of steps presented above. For example, the process 200 can further include a step of generating an error signal in response to the comparison at step 226.

Figure 4:
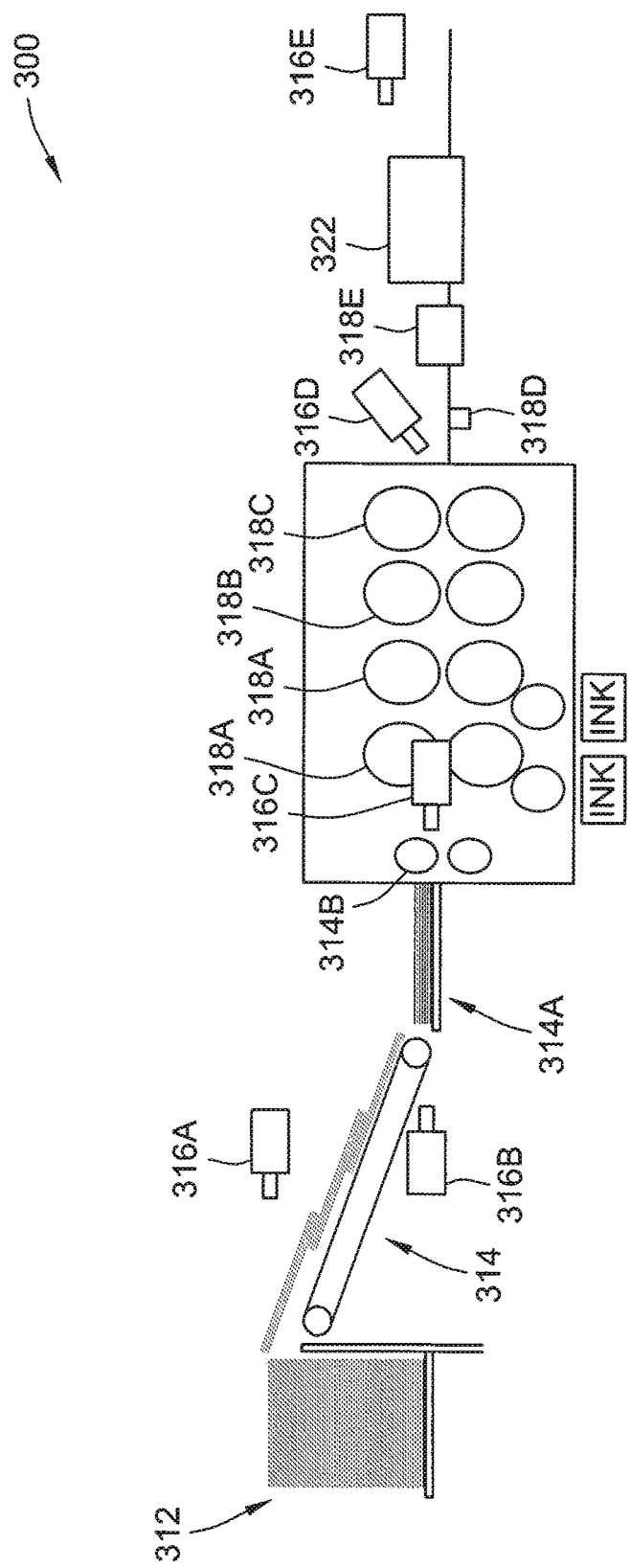
FIG. 4 is a diagrammatic illustration of another example of a sheet processing system according to aspects of the present disclosure.

As described above, the systems and methods of the present disclosure can obtain a plurality of images of the sheets at two different points in a manufacturing process from which measurements and determinations can be made as to the effect of the manufacturing process (or aspects thereof) on the sheets while being transported through the system. According to some additional and/or alternative aspects of the present disclosure, more than two image capture devices can be employed in the system 100. For example, FIG. 4 illustrates an example sheet processing system 300 in which five image capture devices 316A-316E are employed. In the illustrated example, the system 300 includes a flexo folder gluer having an input receptacle 312 containing a stack of corrugated board sheets, a transport mechanism 314, an impression roller 318A, scoring shafts 318B, slotting shafts 318C, a folding section 318D, an adhesive section 318E, and an output receptacle 322. Additionally, as shown in FIG. 4, the system 300 includes a first image capture device 316A, a second image capture device 316B, a third image capture device 316C, a fourth image capture device 316D, and a fifth image capture device 316E. The image capture devices 316A-316E are configured to capture respective images of one or more sheets of corrugated board at different points along the transport path as described above. For example, the first image capture device 316A is configured to obtain an image of one or more sheets as the sheet(s) are received from the input receptacle 312 in the transport mechanism 314A, the second image capture device 316B is configured to obtain an image of one or more sheets as the sheet(s) are received in a feed section 314A, the third image capture device 316C is configured to obtain an image of one or more sheets after the sheet(s) have passed through feed rolls 314B, the fourth image capture device 314D is configured to obtain an image of one or more sheets after the sheet(s) pass through the impression rolls 318A, the scoring shafts 318B, and the slotting shafts 318C, and the fifth image capture device 316E is configured to obtain an image of one or more sheet(s) as the sheet(s) are received in the output receptacle 322.

Accordingly, in the illustrated example, the impact of all manufacturing processes within the system 300 can be determined based on the image obtained by the first image capture device 316A and the image obtained by the fifth image capture device 316E; however, the images obtained by the second image capture device 316B, the third image capture device 316C, and/or the fourth image capture device 316D could additionally and/or alternatively be utilized to determine the impact of a subset of manufacturing processes of the flex folder gluer. For example, the impact of the feeder section 314A can be determined based on the images obtained by the second image capture device 316B and third image capture device 316C. As another example, the impact of the impression rolls 318A, the scoring shafts 318B, and the slotting shafts 318C can be determined based on the images obtained by the third image capture device 316C and the fourth image capture device 316D. As yet another example, the impact of the feed section 314A, the impression rolls 318A, the scoring shafts 318B, and the slotting shafts 318C can be determined based on the images obtained by the second image capture device 316B and the fourth image capture device 316D.

It should be understood that the images obtained by the image capture devices 316A-316E can be analyzed by a controller (e.g., the controller 124) to determine caliper measurement(s) and/or change in caliper measurements (i.e., process-impact information) and compare such process-impact information to one or more threshold values and/or tolerance ranges (i.e., error checking criteria). It also should be understood that the number and locations of the image captured devices illustrated in FIG. 4 is intended as one non-limiting example. According to additional and/or alternative aspects, the system 300 can include more or fewer image capture devices 316A-316E and the image capture devices 316A-316E can be located at locations other than those illustrated in FIG. 4.

Advantageously, the systems and methods of the present disclosure can accommodate high speed manufacturing processes such as those generally desired for the manufacture of products from corrugated board sheets. The systems and methods of the present disclosure can capture and analyze large quantities of data in real time. Because the images can be captured and analyzed rapidly, the systems and methods of the present disclosure can provide a nearly continuous measurement of caliper. As a result, hundreds or thousands of unique data points can be obtained per order, providing real-time feedback to the equipment operators and validation statistics to the customer. For example, the systems and methods of the present disclosure can alert the machine operators if conditions have changed in their incoming stock and allow them to adjust the manufacturing process devices 118 during the run to account for such changes. In some instances, the adjustments may mitigate wear and tear on the manufacturing process devices 118. In other instances, the adjustments can be made to minimize board damage from the process itself.

Figure 5:
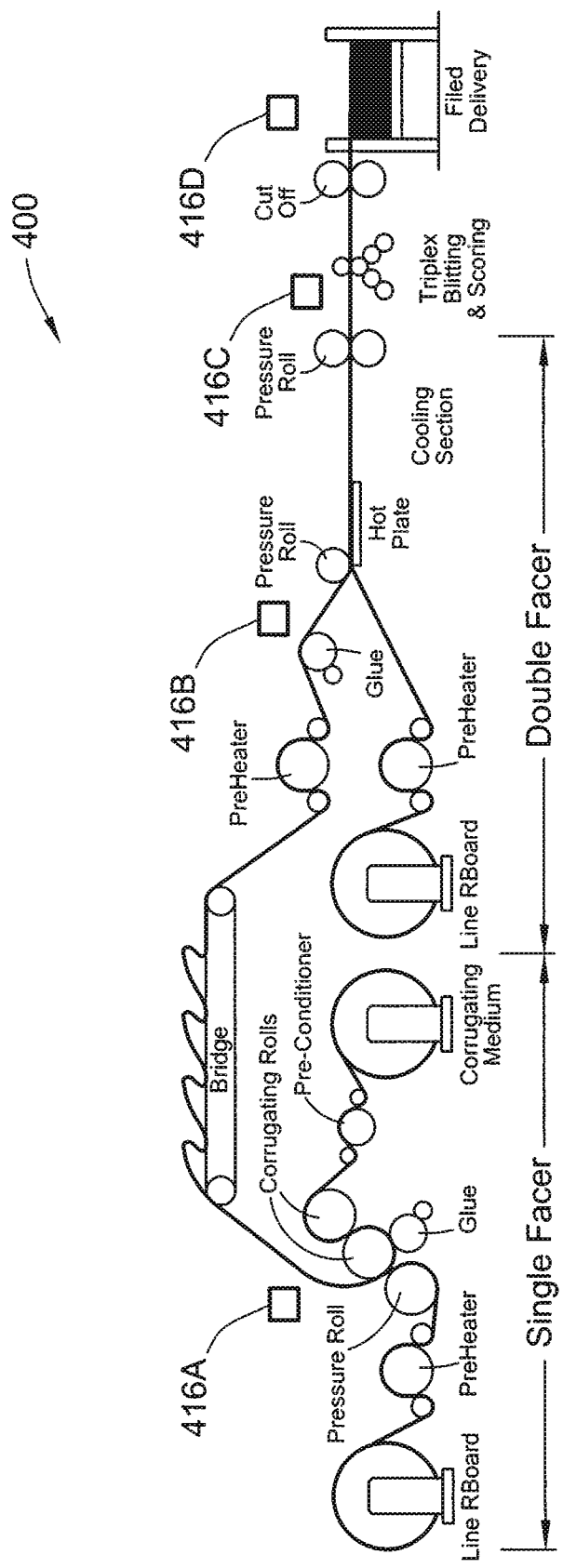
FIG. 5 is a diagrammatic illustration of yet another example of a sheet processing system according to aspects of the present disclosure.

While the embodiments described above relate to systems and methods for processing previously formed sheet material, according to additional and/or alternative aspects of the present disclosure, similar systems and methods can also be configured to determine the impact of manufacturing processes during the production of the sheets. For example, FIG. 5 illustrates an example system 400 including a corrugator for producing the corrugated board sheets. As shown in FIG. 5, the corrugator includes a plurality of unit processes or sections for manufacturing aspects of a plurality of corrugated board sheets. The system 400 further includes a plurality of image capture devices 416A, 416B, 416C, 416D located at various different points in the system 400. Similar to the systems 100, 300 and methods 200 described above, the image capture devices 416A-416D of the system 400 can be configured to obtain images, which can be analyzed (e.g., by a controller) to determine the impact of one or more manufacturing processes. For example, comparing the images obtained by the image capture device 416B and the image capture device 416A can provide a measure of the change in the structure of a fluted singleface web before a second liner is applied, and identify damage done on a bridge in transit. As another example, the images from the image capture devices 416B and 416C can be compared to determine the impact of one or more hot plates. As yet another example, the images from the image capture devices 416C and 416D can be compared to determine the impact of the slitting, scoring, and cutting processes. As still another example, a caliper measurement can be determined from any one of the image capture devices 416A-416D to determine an impact of a manufacturing process. It should be understood that the images obtained by the image capture devices 416A-416D can be analyzed by a controller (e.g., the controller 124) to determine caliper measurement(s) and/or change in caliper measurements (i.e., process-impact information) and compare such process-impact information to one or more threshold values and/or tolerance ranges (i.e., error checking criteria).

The present disclosure includes systems having controllers for providing various functionality to process information and determine results based on inputs. Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller 124 may be a programmable processing device, such as an external conventional computer or an on-board field programmable gate array (FPGA) or digital signal processor (DSP), which executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed:

1. A system for processing a plurality of sheets of material, the system comprising:
   an input configured to receive the plurality of sheets of material;
   an output;
   a transport mechanism configured to transport the plurality of sheets of material, one sheet at a time, from the input along a transport path to the output;
   a manufacturing process device disposed along the transport path and configured to change each of the plurality of sheets of material from a first state to a second state;
   a first image capture device configured to obtain one or more first images, each of the one or more first images being of at least one of the plurality of sheets of material; and
   at least one processor communicatively coupled to the first image capture device, the at least one processor being configured to determine process-impact information based on the one or more first images, the process-impact information including at least a caliper measurement of each of the at least one of the plurality of sheets of material wherein a change in caliper is determined by the difference between the first caliper measurement of each of the at least one of the plurality of sheets of material and a second caliper measurement.

2. The system of claim 1, wherein the at least one processor is further configured to determine whether an error condition exists based on the process-impact information and one or more error checking criteria.

3. The system of claim 1, wherein the first image capture device is positioned adjacent the transport mechanism along the transport path and oriented such that each of the first images includes a lateral side of each of the plurality of sheets of material.

4. The system of claim 1, wherein the first image capture device is positioned adjacent the transport mechanism generally orthogonal to the transport path.

5. The system of claim 1, wherein the plurality of sheets of material comprises corrugated fiberboard.

6. The system of claim 1, wherein the process-impact information is determined by the at least one processor, at least in part, by comparing the one or more first images of the first image capture device with a previously measured set of satisfactory caliper measurements.

7. A method for processing sheet material, the method comprising:
   receiving a plurality of sheets of material;
   transporting, via a transport mechanism, the plurality of sheets of material, one sheet at a time, past a first image capture device;
   obtaining, via the first image capture device, one or more first images of a first set of one or more of the plurality of sheets of material while the plurality of sheets of material is transported past the first image capture device one sheet at a time;
   determining, via at least one processor, a first caliper measurement of the first set of one or more of the plurality of sheets of material based on the one or more first images of the first set; and determining a change in caliper is determined by the difference between the first caliper measurement of each of the at least one of the plurality of sheets of material and a second caliper measurement.

8. The method of claim 7, further including determining whether an error condition exists based on the process-impact information and one or more error checking criteria.

9. The method of claim 7, wherein the first image capture device is positioned adjacent the transport mechanism along the transport path and oriented such that each of the first images includes a lateral side of each of the plurality of sheets of material.

10. The method of claim 7, wherein the first image capture device is positioned adjacent the transport mechanism generally orthogonal to the transport path.

11. The method of claim 7, wherein the plurality of sheets of material comprises corrugated fiberboard.

12. The method of claim 7, further including determining process-impact information by the at least one processor, at least in part, by comparing the one or more first images of the first image capture device with a previously measured set of satisfactory caliper measurements.

* * * * *